United States Patent
Curry et al.

[11] Patent Number: 6,156,268
[45] Date of Patent: Dec. 5, 2000

[54] OZONE DISTRIBUTION IN AN ENCLOSED SPACE

[75] Inventors: Millard R. Curry; Albert M. Curry, both of Jay, Okla.

[73] Assignee: Ozone Environmental Concepts, Inc., Jay, Okla.

[21] Appl. No.: 09/082,635

[22] Filed: May 21, 1998

[51] Int. Cl.[7] .................................................. A61L 9/015
[52] U.S. Cl. ............................ 422/4; 422/129; 422/306; 422/186.07
[58] Field of Search .................................. 422/4, 5, 120, 422/121, 123, 124, 305, 306, 900, 186, 186.07, 186.08; 222/1, 190

[56] References Cited

U.S. PATENT DOCUMENTS

| | | |
|---|---|---|
| 1,714,562 | 5/1929 | Keiser . |
| 1,943,426 | 1/1934 | Fischer et al. . |
| 3,294,480 | 12/1966 | Potapenko . |
| 3,633,547 | 1/1972 | Stevens et al. . |
| 3,884,804 | 5/1975 | Robinson et al. ........................ 422/5 |
| 4,107,268 | 8/1978 | O'Neill et al. ........................ 423/210 |
| 4,528,612 | 7/1985 | Spengler ............................... 361/213 |
| 4,542,434 | 9/1985 | Gehlke et al. ......................... 361/231 |
| 4,909,996 | 3/1990 | Uys ..................................... 422/186.07 |
| 5,010,777 | 4/1991 | Yehl et al. ............................ 73/864.81 |
| 5,160,481 | 11/1992 | Weaver ............................... 422/186.07 |
| 5,195,922 | 3/1993 | Genco ................................. 454/57 |
| 5,514,345 | 5/1996 | Garbutt et al. ......................... 422/124 |
| 5,607,647 | 3/1997 | Kinkead ............................... 422/122 |
| 5,626,820 | 5/1997 | Kinkead et al. ....................... 422/122 |
| 5,664,995 | 9/1997 | O'Keefe ............................... 454/58 |
| 5,704,833 | 1/1998 | Reix et al. ............................ 454/187 |
| 5,788,930 | 8/1998 | McMurray ........................... 422/121 |
| 5,924,597 | 7/1999 | Lynn .................................... 422/124 |

*Primary Examiner*—Terrence R. Till
*Attorney, Agent, or Firm*—William R. Sharp

[57] ABSTRACT

An ozone distribution system is herein described for an enclosed space defined within an enclosure having at least one vent through which gases can escape from the enclosed space. The system comprises: a first tube having an interior and extending through at least a portion of the enclosed space; at least one diffuser integrally connected to the first tube, having an interior in communication with the interior of the first tube, and also having a plurality of spaced outlets; a second tube having at least one outlet positioned in the interior(s) of the diffuser(s); an ozone generator for generating ozone and establishing a flow thereof through the second tube to and through the outlet(s) of the second tube such that ozone is released into the interior(s) of the diffuser(s); and an air intake fan for taking in air from outside the enclosed space and establishing a flow thereof through the interior of the first tube, into the interior(s) of the diffuser(s), and through the outlets of the diffuser(s) so as to carry ozone therewith for distribution in the enclosed space. According to another aspect of the invention, an ozone distribution method uses the above-described tubes and ozone generator to distribute ozone in an enclosed space. Preferably, the enclosed space is maintained at a pressure above that pressure outside the enclosed space.

10 Claims, 2 Drawing Sheets

OZONE DISTRIBUTION IN AN ENCLOSED SPACE

BACKGROUND OF THE INVENTION

The invention relates to the distribution of ozone in an enclosed space, such as that defined within an animal confinement building for animals such as hogs, poultry, etc.

An animal confinement building typically has high concentrations of noxious gases, such as ammonia, hydrogen sulfide, and methane. Such noxious gases result from the decomposition of animal waste products, and can adversely affect the physiology of the animals (particularly ammonia) to thereby result in low production and/or growth. Highly discomforting odors are also associated with such noxious gases. Pathogen-carrying airborne particles, predominantly dead skin cells, are also commonly present in an animal confinement building. The pathogens, including bacteria and viruses, can cause diseases in the animals when the particles are inhaled.

Heretofore, exhaust fans have been used to reduce the concentrations of noxious gases in animal confinement buildings. However, as noxious gases rise from decomposing waste products on the floor of a building, the exhaust fans cause such rising gases to flow directly over the animals before being exhausted from the building. Moreover, exhaust fans increase the cost of heating and cooling the building. Disinfectant chemicals have commonly been used to destroy pathogens. Such chemicals have a number of drawbacks, including high cost and the dangerous possibility of such chemicals finding their way into the food chain and contaminating pork, poultry, and other animal food stuffs which are later consumed by humans.

SUMMARY OF THE INVENTION

It is, therefore, an object of the invention to provide a system and method for effectively controlling noxious gases and pathogens in an enclosed space, such as that defined in an animal confinement building, without using exhaust fans or disinfectant chemicals.

It is also an object of the invention to provide a system and method which employ ozone as an agent to oxidize noxious gases to harmless by-products (i.e. ammonia to nitrogen, water, and diatomic oxygen). Such oxidation also has the beneficial effect of destroying pathogens.

The above objects are realized by an ozone distribution system for an enclosed space defined within an enclosure having at least one vent through which gases can escape from the enclosed space, said ozone distribution system comprising: a first tube having an interior and extending through at least a portion of the enclosed space; at least one diffuser integrally connected to the first tube, having an interior in communication with the interior of the first tube, and also having a plurality of spaced outlets; a second tube having at least one outlet positioned in the interior(s) of the diffuser(s); an ozone generation means for generating ozone and establishing a flow thereof through the second tube to and through the outlet(s) of the second tube such that ozone is released into the interior(s) of the diffuser(s); and an air intake means for taking in air from outside the enclosed space and establishing a flow thereof through the interior of the first tube, into the interior(s) of the diffuser(s), and through the outlets of the diffuser(s) so as to carry ozone therewith for distribution in the enclosed space.

According to another aspect of the invention, there is provided a method for distribution of ozone in an enclosed space defined within an enclosure having at least one vent as described above, said method comprising: providing a first tube, at least one diffuser, and a second tube as previously described; generating ozone and establishing a flow thereof through the second tube to and through the outlet(s) of the second tube such that the ozone is released into the interior (s) of the diffuser(s); and establishing a flow of air from outside the enclosure and through the interior of the first tube, into the interior(s) of the diffuser(s), and through the outlets of the diffuser(s) so as to carry ozone therewith for distribution in the enclosed space.

The pressure in the enclosed space is preferably maintained substantially constant and only slightly above that pressure outside the enclosure. A proper combination of substantially constant air intake flow and vent size will result in this desired pressure condition.

The invention enables effective and uniform distribution of ozone throughout the enclosed space, preferably in conjunction with the above-mentioned pressure condition to thereby allow ozone flow to be adjusted to a substantially constant rate at which a desired ozone concentration is achieved with optimally efficient use of the ozone.

DETAILED DESCRIPTION OF THE INVENTION

Figure 1:
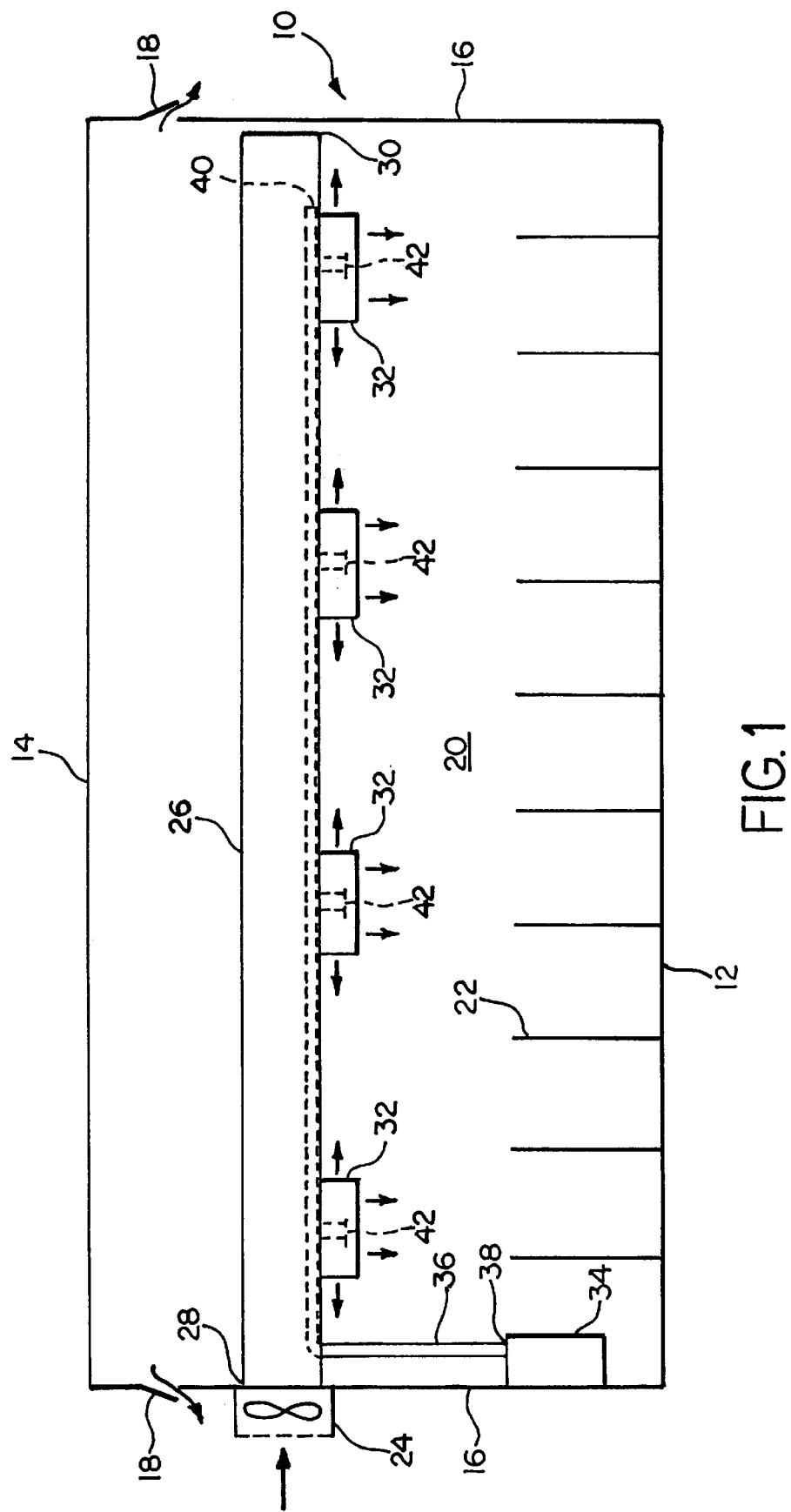
FIG. 1 is a schematic representation of a hog confinement building equipped with a system in accordance with the invention.

Referring to FIG. 1, a hog confinement building, such as a nursery or finisher, is schematically indicated at 10. Building 10 comprises a floor 12, a ceiling or roof 14, and walls 16 having louvered vents 18. Defined within building 10 is an enclosed space 20. A number of partitions, such as indicated at 22, are spaced along floor 12. Hogs (not shown) are kept between the partitions. Of course, the invention as herein described could be applied to enclosures other than the illustrated hog confinement building.

An air intake fan 24 is mounted to a wall 16. Air intake fan 24 can optionally have an associated filter (not shown) for filtering out particles from the air. A tube 26 has an intake end 28, adjacent to air intake fan 24, and a closed end 30 such that the tube extends substantially across enclosed space 20 between ends 28 and 30. Although only one tube is shown in the schematic of FIG. 1, additional tubes could be employed if desired, depending primarily on the dimensions of building 10. A plurality of diffusers 32 are substantially evenly spaced along tube 26 between intake end 28 and closed end 30.

An ozone generator, as schematically indicated at 34, is shown as being mounted to a wall 16. Ozone generator 34 can be of a type which is commercially available, such as from Envirozone Systems Corp. of Monett, Mo. Ozone generator 34 takes in air and converts oxygen therein to ozone. The resulting ozonated air is expelled through an outlet port by an internal fan. The output flow of ozonated air can be adjusted to a desired level. Tube 36 has an intake end 38 connected to the outlet port of ozone generator 34, and extends into and through tube 26 to a closed end 40. Tube 36 has a plurality of outlets 42 (hereafter referred to as tube outlets), between intake end 38 and closed end 40, corresponding to the plurality of diffusers 32. Each diffuser 32 has an associated tube outlet 42.

Figure 2:
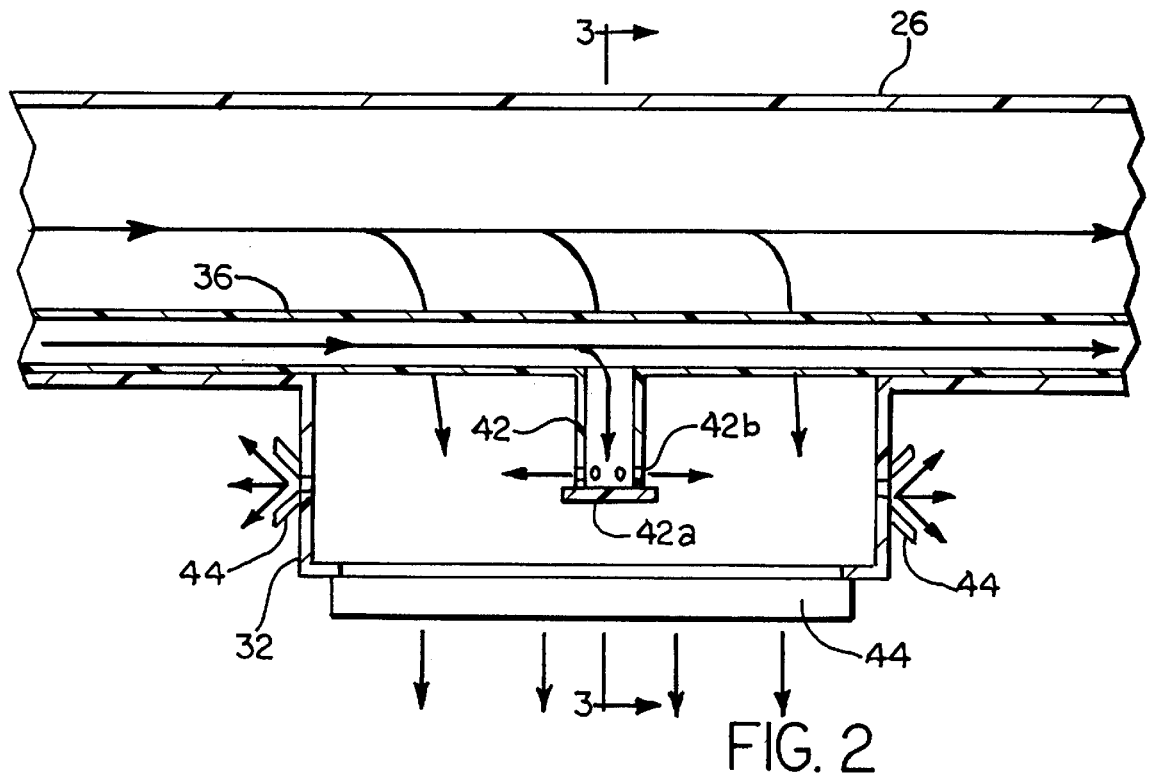
FIG. 2 is a longitudinal cross-sectional view of a portion of the system shown schematically in FIG. 1.
Figure 3:
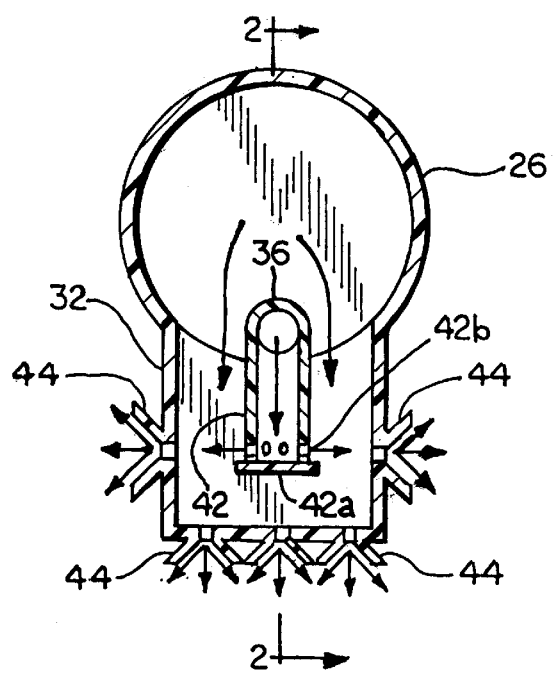
FIG. 3 is a transverse cross-sectional view of the above-mentioned portion of the system.

Referring to FIGS. 2 and 3, these cross-sectional views show details of a single diffuser 32 and its corresponding tube outlet 42. Diffuser 32 is integrally connected to tube 26 so that the interior of diffuser 32 is in communication with the interior of tube 26. The term "integrally connected" means that diffuser 32 can be fixedly connected to tube 26 by any suitable means, or that diffuser 32 can be integral with tube 26. As shown, diffuser 32 has a plurality of spaced and preferably louvered outlets 44. Tube outlet 42 radially extends from tube 36 into the interior of diffuser 32 so as to be substantially centrally positioned therein, and has a cap 42a at its lower end with circumferentially spaced apertures 42b closely adjacent thereto.

With regard to materials of construction, tube 26, diffusers 32, tube 36, and tube outlets 42 are preferably composed of a substantially rigid plastic or plastics which will not react with ozone. Polyvinyl chloride is one example of a suitable plastic.

The operation of the illustrated system will now be described. Arrows indicate gas flow.

Ozone generator 34, as shown in FIG. 1, establishes a flow of 25 ozonated air through tube 36, as shown in FIG. 2. As shown in FIGS. 2 and 3, with respect to a single diffuser 32 and its corresponding tube outlet 42, the ozonated air flows into tube outlet 42 and outwardly through apertures 42b so as to be released into the interior of diffuser 32. Air intake fan 24, as shown in FIG. 1, takes in air from outside building 10 and establishes a flow thereof through tube 26, as shown in FIG. 2. As shown in FIGS. 2 and 3, with respect to a single diffuser 32, the air flows into the interior of diffuser 32 and through diffuser outlets 44 so as to carry ozone therewith. Accordingly, and as shown in FIG. 1, air and ozone will be distributed by each of diffusers 32 in enclosed space 20.

In operation, the interiors of tubes 26 and 36 become pressurized so that the flow of ozonated air from each tube outlet 42 is substantially equivalent and the flow of air into the interior of each diffuser 32 is substantially equivalent. Therefore, the flow of ozone and air from each diffuser 32 is substantially equivalent, and since diffusers 32 are substantially evenly spaced, the air and the ozone as carried by the air are uniformly distributed in enclosed space 20. As previously discussed, the ozone oxidizes noxious gases to form harmless by-products, and such oxidation destroys pathogens carried by airborne particles. Various gases, including the components of air, oxidation by-products, and any small amounts of unreacted ozone and unreacted noxious gases, escape enclosed space through vents 18, as indicated in FIG. 1. Some airborne particles may also pass through vents 18.

Preferably, a proper combination of substantially constant air intake flow and vent sizes maintain a substantially constant pressure in enclosed space 20 which is slightly above (i.e. 0.2–1 psi) that pressure (i.e. atmospheric pressure) outside building 10. Ozone generator 34 can be adjusted to establish a substantially constant flow of ozonated air which, in conjunction with the above-mentioned constant pressure, maintains a desired ozone concentration in enclosed space 20 (with the hogs therein). The ozone concentration can be easily monitored, preferably in an area and at a height where the hogs are present, with a commercially available hand held gas analyzer. The ozone concentration can be within the broad range of about 0.01–1 ppm, but is more typically in the range of about 0.03–0.1 ppm (where parts in "ppm" are volumetric).

The slow but substantially constant flow of gases from vents 18, resulting from the substantially constant but small "positive" pressure in enclosed space 20, allows the ozone to efficiently oxidize noxious gases and destroy pathogens while minimizing loss of unreacted ozone through vents 18.

The illustrated and above-described system can be used in conjunction with other systems (not shown) to further optimize the environment of enclosed space 20. Such optional additional systems include, but are not limited to: a heat pump (preferably buried for optimum efficiency) to heat and cool enclosed space 20; humidifiers to maintain the humidity in enclosed space 20 at or above 60% to optimize the efficiency of the ozone in destroying pathogens; and ionizers to produce ions for combination with oppositely charged, pathogen-carrying, airborne particles to thereby cause such particles to fall by gravity.

Obviously, many modifications and variations of the present invention are possible in light of the above teachings. For example, although it is preferred that the invention is used in conjunction with a building having structurally rigid walls with one or more vents, one or more sides of the building could comprise curtains around the edges of which gases could escape so as to function as vents. Or, a vent or vents could be incorporated into the roof if the building has no ceiling. It is, therefore, to be understood that within the scope of the appended claims, the invention may be practiced otherwise than as specifically described.

What is claimed is:

1. A system comprising:
   an animal confinement enclosure defining an enclosed space therein and having at least one vent through which gases can escape from the enclosed space;
   a first tube having an interior and extending through at least a portion of the enclosed space;
   at least one diffuser integrally connected to the first tube, having an interior in communication with the interior of the first tube, and also having a plurality of spaced outlets;
   a second tube having at least one outlet positioned in the interior of said at least one diffuser;
   an ozone generation means for taking in air and converting oxygen therein to ozone to thereby produce ozonated air containing ozone, and wherein the ozone generation means establishes a flow of the ozonated air through the second tube to and through said at least one outlet of the second tube such that ozonated air is released into the interior of said at least one diffuser;
   an air intake means for taking in air from outside the enclosed space and establishing a flow thereof through the interior of the first tube, into the interior of said at least one diffuser, and through the outlets of said at least one diffuser so as to carry ozone therewith for distribution of the resulting mixture of air and ozone in the enclosed space; and
   wherein a substantially constant flow rate as can be established by the air intake means and the size of said at least one vent are such that a substantially constant pressure in the enclosed space can be maintained above that pressure outside the enclosure.

2. A system as recited in claim 1 wherein the substantially constant pressure in the enclosed space can be maintained about 0.2–1 psi above that pressure outside the enclosure.

3. A system as recited in claim 1 wherein said at least one diffuser comprises a plurality of diffusers and wherein said at least one outlet of the second tube comprises a plurality of outlets corresponding to the plurality of diffusers.

4. A system as recited in claim 3 wherein the first tube has a first intake end adjacent to the air intake means and a first closed end such that the first tube extends from the first intake end to the first closed end substantially across the enclosed space, and wherein the diffusers are substantially evenly spaced along the first tube between the first intake end and the first closed end.

5. A system as recited in claim 4 wherein the second tube has a second intake end connected to the ozone generation means and a second closed end such that the outlets of the second tube are between the second intake end and the second closed end with each outlet of the second tube being substantially centrally positioned in the interior of its corresponding diffuser.

6. An ozone distribution method comprising:

providing (i) an animal confinement enclosure defining an enclosed space therein and having at least one vent through which gases can escape from the enclosed space, (ii) a first tube having an interior and extending through at least a portion of the enclosed space, (iii) at least one diffuser integrally connected to the first tube, having an interior in communication with the interior of the first tube, and also having a plurality of spaced outlets, and (iv) a second tube having at least one outlet positioned in the interior of said at least one diffuser;

generating ozonated air containing ozone by converting oxygen in air to ozone, and establishing a flow of the ozonated air through the second tube to and through said at least one outlet of the second tube such that the ozonated air is released into the interior of said at least one diffuser;

establishing a flow of air from outside the enclosure and through the interior of the first tube, into the interior of said at least one diffuser, and through the outlets of said at least one diffuser so as to carry ozone therewith for distribution of the resulting mixture of air and ozone in the enclosed space; and wherein a substantially constant flow of air as established through the first tube and the size of said at least one vent are such that a substantially constant pressure is maintained in the enclosed space above that pressure outside the enclosure.

7. A method as recited n claim 6 wherein the pressure in the enclosed space is maintained about 0.2–1 psi above the pressure outside the enclosure.

8. A method as recited in claim 7 wherein the pressure outside the enclosure is atmospheric pressure.

9. A method as recited in claim 6 wherein a substantially constant flow of ozonated air through the second tube is such that, in the pressure conditions of the enclosed space, an ozone concentration in the enclosed space is maintained in the range of about 0.01–1 ppm.

10. A method as recited in claim 6 wherein the first tube extends substantially across the enclosed space, said at least one diffuser comprises a plurality of diffusers substantially evenly spaced along the first tube, and the second tube has a plurality of outlets corresponding to the plurality of diffusers, and wherein the flow of ozonated air from each outlet of the second tube is substantially equivalent and the flow of air into the interior of each diffuser is substantially equivalent, whereby the flow of ozone and air from each diffuser is substantially equivalent such that the air and the ozone as carried by the air is uniformly distributed in the enclosed space.

* * * * *